(12) United States Patent
Chiu

(10) Patent No.: US 9,017,244 B2
(45) Date of Patent: Apr. 28, 2015

(54) ARTIFICIAL INTELLIGENCE AND METHODS OF USE

(75) Inventor: Gordon Chiu, Chatham, NJ (US)

(73) Assignee: Biological Responsibility, LLC, Austin, TX (US)

( * ) Notice: Subject to any disclaimer, the term of this patent is extended or adjusted under 35 U.S.C. 154(b) by 665 days.

(21) Appl. No.: 13/339,824

(22) Filed: Dec. 29, 2011

(65) Prior Publication Data

US 2012/0172661 A1 Jul. 5, 2012

Related U.S. Application Data

(60) Provisional application No. 61/427,813, filed on Dec. 29, 2010.

(51) Int. Cl.
*A61F 5/41* (2006.01)
*A61F 7/00* (2006.01)

(52) U.S. Cl.
CPC . *A61F 5/41* (2013.01); *A61F 7/007* (2013.01); *A61F 2007/0048* (2013.01)

(58) Field of Classification Search
CPC ...... A61F 2/26; A61N 1/36007; A61H 23/02; A61H 19/32; A61H 2201/10; A61H 2201/5002; A61H 2201/5058; A61H 2201/5084; A61H 2230/00; A61H 2230/505; A61H 2230/65; A61H 2201/501
USPC ........................ 600/38–41, 382, 546; 128/897
See application file for complete search history.

(56) References Cited

U.S. PATENT DOCUMENTS

| | | | |
|---|---|---|---|
| 5,473,732 A | 12/1995 | Chang | |
| 6,991,600 B1 | 1/2006 | Wang | |
| 7,527,589 B2 * | 5/2009 | Squicciarini | 600/39 |
| 2003/0069470 A1 | 4/2003 | Lee | |
| 2004/0063833 A1 * | 4/2004 | Chen | 524/270 |
| 2004/0175680 A1 | 9/2004 | Hlavac et al. | |
| 2006/0041014 A1 | 2/2006 | Naylor et al. | |
| 2006/0229494 A1 | 10/2006 | Wu | |
| 2007/0078493 A1 | 4/2007 | Gerber | |
| 2007/0092862 A1 | 4/2007 | Gerber | |
| 2007/0282768 A1 | 12/2007 | Chang | |
| 2008/0065187 A1 | 3/2008 | Squicciarini | |

FOREIGN PATENT DOCUMENTS

CA WO 02/087478 A1 11/2002

OTHER PUBLICATIONS

PCT International Preliminary Report on Patentability; PCT/2011/067789;; Applicant Chiu, Gordon; issued Jul. 2, 2013; 6 pages.
PCT International Search Report and Written Opinion; PCT/2011/064648; dated Jul. 30, 2012.
Walz, J, Perrotte P, et al Ejaculatory disorders may affect screening for prostate cancer, J Urol. Jul. 2007; 178(1):232-7.
Giles, G.G., Severi, G. et al "Sexual factors and prostate cancer"; BJU International; 2003; 92, 211-216.

\* cited by examiner

*Primary Examiner* — Samuel Gilbert
(74) *Attorney, Agent, or Firm* — Gearhart Law, LLC

(57) ABSTRACT

A device that provides a unique surrogate experience by utilizing artificial intelligence and polymeric materials which enables surrogate exchange and/or interaction with the biology of the user. The device may be fit on to the penis of a user to provide stimulation and via sensory wave feedback from an electromusculography system (EMG) have the stimulation varied accordingly. The stimulation may include vibrations, heating, cooling, expanding, or contracting of the device as necessary.

11 Claims, 3 Drawing Sheets

ARTIFICIAL INTELLIGENCE AND METHODS OF USE

CLAIM OF PRIORITY

This application claims the priority of U.S. Ser. No. 61/427,813 filed on Dec. 29, 2010, the contents of which are fully incorporated herein by reference.

FIELD OF THE INVENTION

The invention relates to a device for a unique surrogate experience utilizing artificial intelligence and polymeric materials which enable surrogate exchange and/or interaction with the biology of the user. Medical utility and benefits are also discussed.

BACKGROUND OF THE INVENTION

The present invention relates to a device providing a unique surrogate experience utilizing artificial intelligence and polymeric materials which enable surrogate exchange and/or interaction with the biology of the user, and its medical utility and benefit.

The invention has many uses for the user including providing a virtual sexual experience of the user, assisting in the treatment of underlying medical urological conditions, improving poor sexual function associated with disease or in diagnosing male infertility. Such known medical conditions which may be treated or diagnosed utilizing this invention include, but are not limited to: erectile dysfunction, premature ejaculation, hypogonadism and male infertility. Some literature suggests that increasing ejaculation frequency may have a negative corollary with subsequent development of prostate cancer.

Erectile dysfunction (ED) is prevalent in men aged 40 to 70 years and increases with age. Population studies estimate that 10 to 20 million men suffer ED, and 30 million men suffer at least partial ED. In years past, impotence was frequently attributed to psychological causes (psychogenic ED), but today, at least 80% of ED is likely due to physiologic causes such as vascular (decreased arterial blood flow or venous insufficiency), neurologic (nerve injury following surgery or neurologic diseases), or endocrine (hormone) abnormalities.

In the past, men have been inclined to suffer ED without seeking medical evaluation or treatment. Today, due to the increase in public awareness and the advent of several treatment options, men with ED are more likely to seek treatment that offers opportunity to regain sexual function and restitution of an important quality of life activity.

Premature ejaculation (ejaculation occurring sooner than the male or his partner would want) occurs in up to one third of adult men. Men may be reluctant to seek evaluation or treatment for this problem and consequently they and their partner may suffer frustration and anxiety which detracts from their sexual experience and their quality of life. In some men, premature ejaculation may be associated with erectile dysfunction.

Primary premature ejaculation indicates that the condition has been present from the onset of sexual activity. Secondary premature ejaculation denotes the onset after some period of satisfactory sexual activity without ejaculatory problems.

Hypogonadism is defined as little or no secretion of sex gland hormones. In men, this is essentially a failure of the testes to secrete the male hormone testosterone that is responsible for male development including sexual maturation at the time of puberty and becoming fertile due to sperm production in the testes. Primary hypogonadism indicates that the male has never produced enough testosterone to provide normal blood levels. This might be due to genetic abnormalities such as Klinefelter's syndrome. Besides genetic causes, other factors that contribute to secondary hypogonadism include tumors, surgery, radiation exposure, infections, trauma/bleeding, nutritional deficiencies, or iron excess (iron deposits in the liver known as hemochromatosis). Testosterone production in the testes depends upon the production of Leutinizing Hormone (LH) which is secreted from the pituitary gland. When testosterone blood levels are low, LH secretion increases leading to increased testosterone production. When serum levels of testosterone reach normal levels, LH production decreases.

Approximately 15% of couples have difficulty conceiving, and in these instances, male subfertility is the primary factor in 30% and a secondary factor in 20%. Therefore, the male is a contributing factor in 50% of infertility cases.

Fertility evaluation is traditionally recommended for couples who fail to conceive after one year of unprotected intercourse. Evaluation of the male partner should be performed first because initial exam and testing is non-invasive and less expensive than the fertility evaluation of the female partner.

The evaluation of the male partner begins with a thorough history to identify risk factors such as previous chemotherapy or radiation exposure, steroid, alcohol or other drug use, and injuries that could contribute to sub fertility. A physical exam seeks to identify anatomic abnormalities such as varicocele or an abnormal vas deferens. Basic laboratory testing that includes two semen analyses and blood tests for hormone abnormalities completes the initial exam.

Some or all of these conditions may be treated with the device of this invention, especially with the guidance of medical care and/or therapy, thereby avoiding side effects of oral medication such as Viagra®, Levitra® and Cialis®, avoiding invasive surgery such as penile implants and insertion of medication into the urethra or injection into the penis glands.

WO/2002/087478 relates a male sexual aid having the general shape of a condom, but which is loose fitting and which has a tail for insertion between the buttocks of the user in order to retain the device in place. It lacks the virtual experience provided by the device of this invention.

United States Patent Application 20060041014 relates to the use of neutral endopeptidase inhibitors (NEPi) and a combination of NEPi and phosphodiesterase type 5 (PDE5) inhibitor for the treatment of male sexual dysfunction, in particular erectile dysfunction. Medications such as this have untoward side effects.

U.S. Pat. No. 6,991,600 is a male sexual aid that is made of soft and elastomeric material such as rubber, silicone rubber, or latex. The device is composed of a hollow tube and two rings arranged on two lateral sides thereof. The hollow tube (tubular cone body) has only one opening for accommodating a micro-vibrator or LED capsule. The device does not interface with the electronic devices, as do the devices of this invention.

U.S. Pat. No. 6,793,620 relates to a prosthesis for male sexual aid comprising a semi-rigid sleeve of thermoplastic material and two straps of elastomeric material. The sleeve has a cutout along its whole length and is shaped outside in three portions: a head, a shaft, and a base.

International Patent Application Publication WO/2008/067487 describes a hand-held or hand-attached computer control device and associated system that is utilized to control graphical objects in a computer-driven display in which the motion, type of behavior, and attributes of the graphical object are controlled through movement and resulting accelerations of the control device. A mouse and computer are required to use the device.

United States Patent Application 20090234182 relates to a system comprising segmented sexual aid tools comprising a plurality of interchangeable components, all of which fit together so that a user may customize the shape, girth and length of the sexual aid tool. The system further comprises monetization and internet sales in e-commerce of sexual aid tools utilizing custom orders and rapid fabrication of such interchangeable components. Production of tools may be computer driven.

SUMMARY OF THE INVENTION

The invention is a device to stimulate a penis and to electronically detect sensory waves from the penis of a user via an electromusculography system (EMG). The device has a polymeric sleeve formed to fit on the head and the shaft of the penis, a power source, and a detector. A plurality of electrodes are mounted on the polymeric sleeve, wherein each electrode has a plurality of elastic flexible fingers, each having a free end portion with a conductive tip at the end of each finger, with the conductive tip making contact with the head of the penis to collect electrical signals from the penis, and a conductive moiety to conduct electrical signals from the conductive tip to the detector.

The present invention allows a user to stimulate his penis, and if so desired, to collect data that may be used to aid in overcoming a variety of medical conditions. The device may be programmed to aid a user to follow a set pattern so that he trains his body and thus achieves his desired health goals.

It is an object of the invention to provide stimulation to a user's penis.

It is an object of the invention to receive feedback from a user's penis in order to improve performance.

It is an object of the invention to use data obtained during stimulation of the penis to train the user's body.

It is an object of the invention to use data obtained from brain waves to achieve physical objectives.

It is an object of the invention to provide target wave patterns for the user to follow to achieve his physical objectives.

It is an object of the invention to treat or diagnose a urinary tract infection.

DESCRIPTION OF THE PREFERRED EMBODIMENTS

Figure 1:
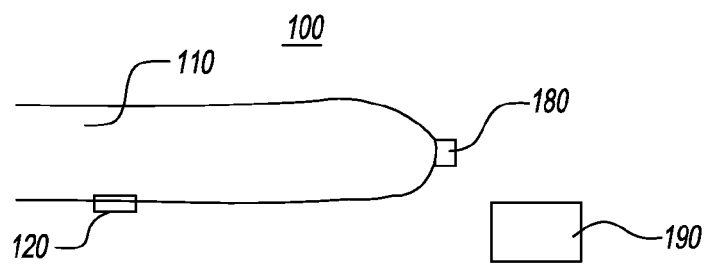
FIG. 1 is a side view of the invention.

FIG. 1 is a side view of the invention. FIG. 1 shows the electromusculography system (EMG) 100 and the polymeric sleeve 110, power source 120, detector 180, and data collection device/controller 190. The polymeric sleeve has been formed to fit on the head and the shaft of a penis. The polymeric sleeve is made of an elastic material that can be adapted to stretch and fit any penis. The polymeric sleeve may be made of or include portions of any material, including but not limited to, elastomeric gels, elastomers, rubbers, plastics, thermoplastic elastomers, metals, wood and paper, skin, fluids, or any other material or combination of materials. A preferred material for the polymeric sleeve is an elastomeric gel formed by mixtures of 5%-9% by weight of block copolymer and 90%-95% by weight of plasticizing oil. Any block copolymer may be used; the preferred block copolymer is a mixture of styrene ethylene butylene styrene (SEBS) block copolymer and styrene ethylene propylene styrene (SEPS) block copolymer. Any plasticizing oil may be used; the preferred plasticizing oils are mineral oil, synthetic oil, petrolatum naphthenic oil, synthetic polybutene, and synthetic polypropylene.

The power source may be any power source that supplies electrical current, including but not limited to, a battery, a connection to a wall outlet, or other. The power source may power the device through a switch on the device; there may be multiple switches so that one part of the device may be used while the other parts are not used.

The detector may be any detector that detects electrical signals, including but not limited to, an electrometer, a current sensor, a voltage detector, a galvanometer, a Hall Effect Sensor or any other detector that will detect and measure the signal generated by the EMG device. The detector may employ amplifiers and other methods to increase the signal strength to make it easier to measure.

Figure 2:
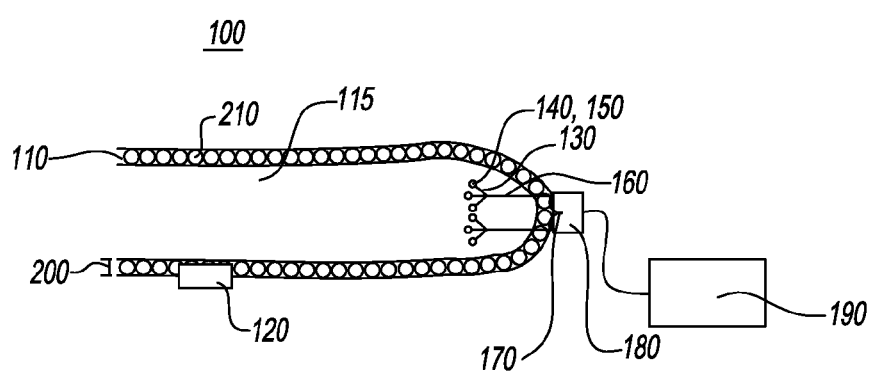
FIG. 2 is a side cut-away view of the invention.

FIG. 2 is a side cut-away view of the invention. FIG. 2 shows the electromusculography system (EMG) 100, polymeric sleeve 110, polymeric sleeve inner surface 115, power source 120, non-conductive elastic flexible finger 130, finger free-end portion 140, finger conductive tip 150, electrode 160, conductive moiety 170, detector 180, data collection device/controller 190, the polymeric sleeve wall thickness 200, and flexible elements 210.

The polymeric sleeve 110 fits over a user's penis. A user puts it on, then the device is started. The power source 120 provides power to vibrate the flexible elements 210 in the wall of the polymeric sleeve 110, thereby stimulating the penis. The finger conductive tip 150 contacts the penis and collects electrical signals which are transmitted through the electrode 160 to the detector 180. The data is then transmitted to the data collection device/controller 190. Conductive fluid may be applied to the penis to facilitate collection of the electrical signals.

Although the device is shown with two electrodes, each having three non-conductive elastic flexible fingers 130, with their corresponding finger free-end portions 140 and finger conductive tips 150, there may be any number of electrodes and any number of non-conductive elastic flexible fingers with their corresponding components.

The conductive tips conduct electricity from the penis head to the electrodes, which then send the electrical signal to the detector. The finger free-end portions are the part of the conductive elastic flexible fingers that may move around as necessary to comfortably contact the penis head. The other ends of the conductive elastic flexible fingers are anchored to the electrodes. The conductive moiety facilitates transferring the signal from the electrodes to the detector; it may contain amplifiers or other electronics.

The polymeric sleeve inner surface 115 is smooth, non-pointed, and non-abrasive to the penis shaft and the penis head. It may be lubricated or dry when the device is in use.

The device may be started and controlled using a controller such as a switch or dial on the power source, or it may be started and controlled by the user or from a remote location using a data collection device/controller 190. The controller may be integral or separate from the data collection device, and they may be operated separately. The data collection device/controller may be wired or wireless. Data from the data collection device may be used to provide feedback to the controller, which may then be adjusted to achieve the desired result.

The data collection device may be any device that can collect data, such as but not limited to, a computer, a mobile phone, or a tablet. This device may also control the electromusculography system (EMG), or the control device could be a separate and different type of device, including but not limited to, a switch or control knob. There may be feedback such that a biofeedback loop is created, with data collected being used to control the device and thus the user's behavior, which feeds back again to collected data. These data may be used to develop an algorithm that can be used to evaluate a user's performance compared to others, and may become a training tool for enhancement.

Figure 3:
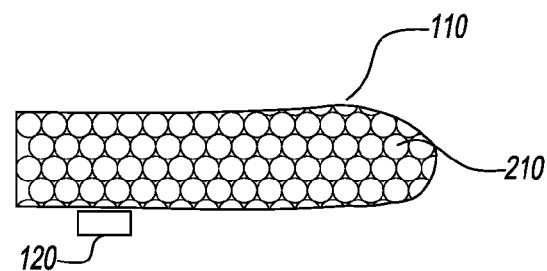
FIG. 3 is a side sectional view of the invention.

FIG. 3 is a side sectional view of the invention. FIG. 3 shows the polymeric sleeve 110, the power source 120, and the flexible elements 210. The flexible elements may be any shape or size, but are preferably round and approximately 2-5 mm in diameter. They may be made of any material, including but not limited to, plastic, rubber, metal, or any filled material, including but not limited to, plastic, rubber or metal filled with water or other fluid.

The flexible elements can be heated or cooled using the power source and the controller, and they may be made to expand or contract. The frequency and intensity of vibration of the flexible elements may also be controlled. This may be desirable to adjust the level of stimulation when a user is trying to train himself to achieve a desired result, for instance, to prevent premature ejaculation. He may initiate his session using a high intensity of vibration and warm flexible elements, for instance, then lower the intensity and temperature of the flexible elements to prevent ejaculation, increasing one or both after a set time period or in response to some other criteria. He may also contract the flexible elements so the sensation is lessened, thus preventing ejaculation. He may cycle through this or any combination of routines a number of times until he trains his body to respond in the desired way.

Alternately, the polymeric sleeve itself may be heated or cooled, and expanded or contracted, either in conjunction with the flexible elements or on its own.

The user may control the characteristics of the flexible elements himself, or he may have someone else, such as a doctor, controlling them. The doctor may adjust the flexible elements based on the feedback from the electrodes and detector that is fed to the data collection device/controller, or there may be set programs that cycle the flexible elements through a set of characteristics.

Figure 4:
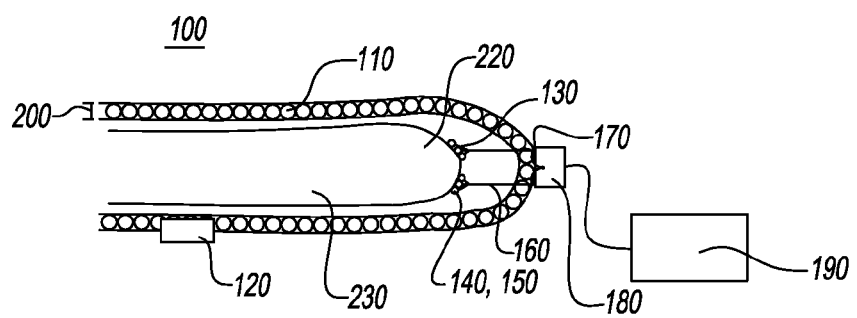
FIG. 4 is side cut-away view of the invention in use.

FIG. 4 is side cut-away view of the invention in use. FIG. 4 shows the electromusculography system (EMG) 100, polymeric sleeve 110, power source 120, non-conductive elastic flexible finger 130, finger free-end portion 140, finger conductive tip 150, electrode 160, conductive moiety 170, detector 180, data collection device/controller 190, polymeric sleeve wall thickness 200, penis head 220, and penis shaft 230.

The penis head 220 contacts the finger free-end portion 140 and the finger conductive tip 150 at the end of the non-conductive elastic flexible finger 130. The flexibility of the non-conductive elastic flexible finger 130 allows the penis head 220 to contact the conductive tip 150 from any close position without causing negative sensation to the penis head 220. The electrical signals are collected and transmitted as described with FIG. 2. Signals may be also be collected from the penis shaft 230 by placing the non-conductive elastic flexible fingers 130 with conductive tips 150 at other positions in the polymeric sleeve 110. Although shown not touching the closed end of the polymeric sleeve, the penis head may be anywhere in that area, including flush against the closed end of the polymeric sleeve. Since the polymeric sleeve is made from an elastomeric material that can stretch, it may form itself to make optimum contact with the penis.

The non-conductive elastic flexible fingers may be longer than shown in the figure, and may extend farther into the polymeric sleeve 110.

In an alternate embodiment, the polymeric sleeve itself may be conductive, such that the non-conductive elastic flexible finger 130, finger free-end portion 140, and finger conductive tip 150 are not necessary. In this case, the signal from the polymeric sleeve may be sent directly to an electrode or to a detector through either wired or wireless methods. The inner surface of the polymeric sleeve may contain a conductive moiety, either along the entire length or at specific data collection points. The electrical signal from this moiety would then be passed to the outside of the polymeric sleeve where it is collected and detected, or it would be detected wirelessly from the inner surface of the polymeric sleeve.

The device may be used as shown with the non-conductive elastic flexible finger, finger free-end portion, finger conductive tip, electrode, detector, conductive moiety, detector, and the data collection device/controller, or none, any or all of these components. For instance, if just used for stimulation, a user may use none of the components. Or, the user may use just the controller with the data collection portion turned off.

Figure 5:
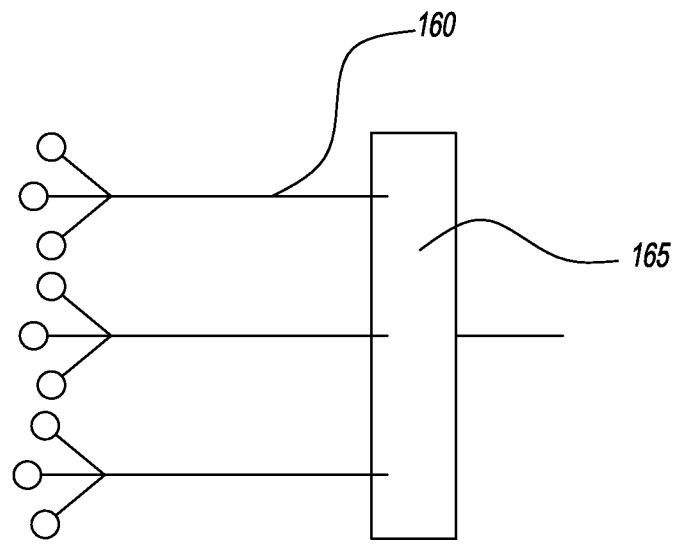
FIG. 5 is an exploded view of a section of the invention.

FIG. 5 is an exploded view of a section of the invention. FIG. 5 shows the electrodes 160 in an electrode holder 165. This may be desirable to keep the electrodes in a certain position for instance, if they aren't collecting electrical signals as expected, they may need to be somewhat immobilized in an electrode holder to facilitate data collection.

Figure 6:
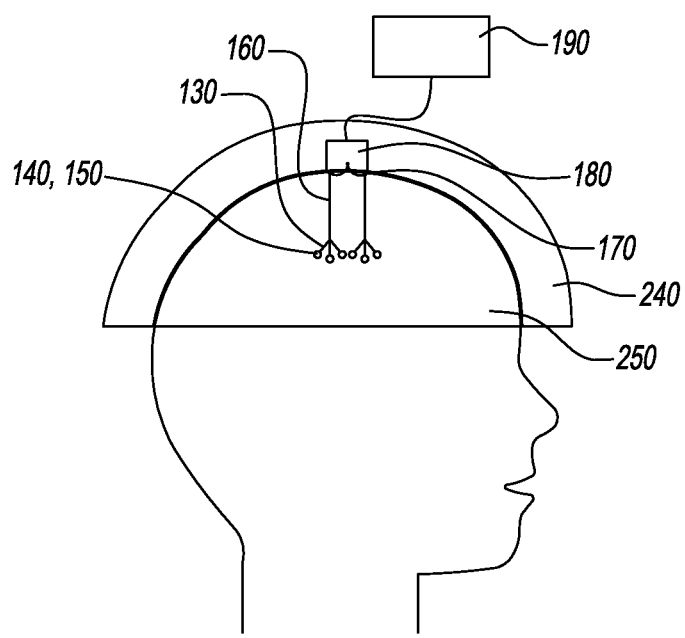
FIG. 6 is a side cut-away view of an alternate embodiment of the invention.

FIG. 6 is a side cut-away view of an alternate embodiment of the invention. FIG. 6 shows the polymeric attachment 240 on a user's head 250. FIG. 6 also shows the non-conductive elastic flexible finger 130, finger free-end portion 140, finger conductive tip 150, electrode 160, conductive moiety 170, detector 180, and data collection device/controller 190. In this case, the electronically detected sensory waves are coming from the head muscles or brain of the user, depending on how the device is configured. EMG waves may be collected using the device in this configuration, or they may be collected using a separate device and may be used in conjunction with the data from this device.

The flexible elements shown in the polymeric sleeve may be present or absent in this embodiment, and, if present, may have different characteristics. The polymeric sleeve of the previous figures may be used in conjunction with this embodiment; the data collected from both embodiments may be used to help a user to train his body and mind to work together to achieve the desired result. It may be placed anywhere on the user's head, or placed as shown in the figure.

The polymeric attachment 240 may be formed or stretchable so that it can fit any part of the user's body; for instance, it may be desirable to measure fist clenching, and the polymer attachment could be placed on the user's hand. This could also be used with data from any other part of the body, either for diagnostic or training purposes.

Figure 7:
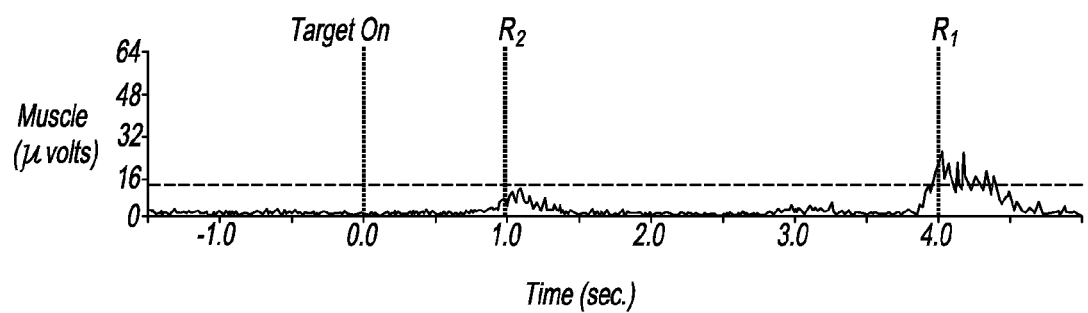
FIG. 7 is a representation of data that may be collected using the invention.

FIG. 7 is a representation of data that may be collected using the invention. FIG. 7 shows a graph of time vs. muscle activity. The device is activated at time zero; in the case of this invention, the flexible elements in the polymeric sleeve would be made to stimulate the penis by vibrating, and heating up, and/or expanding. At time 1.0 seconds, the muscle activity, measured as microvolts, indicates that the user is about to ejaculate, which is premature. In order to delay ejaculation, the flexible elements could be controlled to vibrate less intensely or not at all, could cool down and/or contract. This would remove or reduce the stimulation to the penis, such that ejaculation doesn't occur at that time. The stimulation could be re-introduced after muscle activity has decreased, for instance at 2.0 seconds; this cycle could be repeated as many times as desired until the user is ready to ejaculate. In this instance, the user ejaculates at 4.0 seconds, as measured by the device.

The device could be used to provide a method of conditioning and building stamina in an individual. For instance, a data set of target patterns for responses, such as a set of brain waves and corresponding muscle waves, could be used to train an individual. The penis could be stimulated as described above, then data collection device/controller could be used to provide target wave patterns for responses. The data collection device/controller could receive data from multiple detectors, for instance one associated with a polymeric attachment on the head and one associated with the polymeric sleeve on the penis. The data from both the brain waves and muscle waves could be measured, and as stimulation is provided, targeted responses could be measured and feedback provided (such as reducing stimulation to the penis) to assist the individual in meeting targets (such as delay of premature ejaculation). This could result in prolonged erection times, larger amounts of sperm delivery, and an increase in sexual stamina in the user.

The device could also be devised such that the controller is directed by the user's concentration levels. For instance, the intensity of vibrations of the flexible elements may be modified by the user's concentration levels. This may be achieved by causing an increased level of concentration to result in the creation of greater alpha waves; lowered levels of concentration would result in lesser alpha waves. The alpha waves could influence the intensity of vibrations of the flexible elements.

Thus, using a combination of brain and muscle measurements, a user could train his body to respond in desired ways.

The elastomeric gels of the invention may be prepared by methods known in the art. For example, as formulas disclosed in U.S. Pat. Nos. 4,369,284, 4,618,213, 5,153,254, 5,262,468, 5,334,649, 5,336,708, 5,466,232, 5,806,523, 5,807,360 and 5,782,818 which are incorporated herein by reference in their entirety.

Preferred elastomeric gels are formed by mixtures of 5% to 9% by weight of block copolymer and 90% to 95% by weight of plasticizing oil, and trace amounts of adjunctive agents, such as pigments and fillers. The preferred composition of the polymeric sleeve and polymeric attachment is 99.5% to 98% elastomeric gel compound.

The oils may be therapeutic, and may be added separately from the polymeric sleeve composition. For instance, the composition of the polymeric sleeve may not contain certain desired oils due to thermal restrictions. In this case, the oil could be added separately, through a port or other method into the interior of the polymeric sleeve.

The release of the oils into the interior of the polymeric sleeve may be triggered by certain EMG responses or may be controlled by the controller, either in conjunction with the data collection portion of the device or by the controller portion alone.

Any method may be used to make the polymeric attachment or the polymeric sleeve; the preferred method is molding or extruding the material to yield the desired forms. To such elastomeric gels, active agents may be added prior to extrusion to the preferred shape or placement into a mold or feeding through an extrusion machine.

A preferred embodiment is a method of treating or diagnosing a urological condition present in a user by utilizing a device disclosed herein. The urological condition may be selected from one or more: erectile dysfunction, premature ejaculation, hypogonadism, male infertility, prostate cancer and Peyronie's disease (curvature of the penis).

The invention contemplates advanced IP Chip design for utilization with the device, for example, including but not limited to, a brain chip or external skin chip, for example an EEG or EMG chip. In addition, software development tools and cryogenics may be utilized as part of the invention. The above-mentioned patents, applications, test methods, and publications are hereby incorporated by reference in their entirety. Many variations of the present invention will suggest themselves to those skilled in the art in light of the above detailed description. All such obvious variations are within the fully intended scope of the appended claims.

I claim:

1. A device to stimulate a penis and to electronically detect sensory waves from the penis of a user via an electromusculography system (EMG), the device comprising:
a polymeric sleeve having an outer surface and an inner surface, the polymeric sleeve being formed to fit on the head and shaft of the penis;
a power source operably coupled to the polymeric sleeve;
a plurality of electrodes mounted on the polymeric sleeve, wherein each of the plurality of electrodes comprise a plurality of elastic flexible fingers each having a free end portion with a conductive tip at the end of each finger;
a detector operably coupled to the plurality of electrodes;
a plurality of flexible elements disposed between the outer surface and the inner surface of the polymeric sleeve, wherein the plurality of flexible elements are capable expanding and/or contracting thus causing expanding and/or contracting of the polymeric sleeve; and
a conductive moiety disposed on the inner surface and/or the outer surface of the polymeric sleeve to conduct the electrical signals from the conductive tip to the detector.

2. The device of claim 1, wherein the flexible elements can be heated, cooled, or a combination thereof.

3. The device of claim 1, wherein the polymeric sleeve can be heated, cooled, or a combination thereof.

4. The device of claim 1, wherein the inner surface of the polymeric sleeve is smooth, non-pointed and non-abrasive to the head and shaft of the penis.

5. The device of claim 1, further comprising an electrode holder to be fitted on the polymeric sleeve and to enclose and mount each of the plurality of electrodes.

6. The device of claim 1, further comprising one or more polymeric attachments for attachment to one or more parts of the body of the user.

7. The polymeric attachment of claim 6, wherein the polymeric attachment is configured to fit over and on the head of the user.

8. The device of claim 6, wherein the polymeric sleeve or the polymeric attachment comprise an elastomeric gel formed by mixtures of about 5% to about 9% by weight of block copolymer and about 90% to about 95% by weight of plasticizing oil.

9. The device of claim 8, wherein the block copolymer is selected from styrene ethylene butylene styrene (SEBS) block copolymer and styrene ethylene propylene styrene (SEPS) block copolymer.

10. The device of claim 8, wherein the polymeric sleeve and/or the polymeric attachment comprise about 99.5% to about 98% of the elastomeric gel.

11. The device of claim 6, wherein the polymeric sleeve or the polymeric attachment is capable of conducting electrical impulses.

* * * * *